US00PP33409P2

(12) United States Plant Patent
van Geest

(10) Patent No.: US PP33,409 P2
(45) Date of Patent: Aug. 31, 2021

(54) ***FICUS* PLANT NAMED 'ESFIDECLO1'**

(50) Latin Name: *Ficus elastica*
Varietal Denomination: ESFIDECLO1

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 17/092,245

(22) Filed: Nov. 7, 2020

(51) Int. Cl.
*A01H 5/12* (2018.01)
*A01H 6/00* (2018.01)

(52) U.S. Cl.
USPC ..... Plt./211

(58) Field of Classification Search
USPC ..... Plt./211
See application file for complete search history.

*Primary Examiner* — Susan McCormick Ewoldt
(74) *Attorney, Agent, or Firm* — Samuel R. McCoy, Jr.

(57) ABSTRACT

A new and distinct variety of *Ficus* plant named 'ESFIDECLO1' which is characterized by the combination of an obovate to broad oblong plant profile, an abundance of dark green, glossy foliage, foliage with a light green abaxial surface and a prominent red main vein, and the stability of all characteristics from generation to generation.

3 Drawing Sheets

Latin name of the genus and species: The Latin name of the genus and species of the novel variety disclosed herein is *Ficus elastica.*

Variety denomination: The inventive variety of *Ficus* disclosed herein has been given the variety denomination 'ESFIDECLO1'.

BACKGROUND OF THE INVENTION

Parentage: 'ESFIDECLO1' originated as a naturally occurring, whole-plant mutation of *Ficus elastica* 'Robusta' (not patented). In the summer of 2015, the inventor discovered the mutation at his commercial greenhouse in 's-Gravenzande, the Netherlands, growing amongst a cultivated population of 'Robusta' plants. The mutation was noted for its dark green, glossy foliage and red main veins on the abaxial leaf surface and was subsequently isolated for further evaluation in order to confirm the distinctness and stability of the characteristics first observed. Upon confirmation of distinctness and stability, 'ESFIDECLO1' was selected for commercialization.

Asexual Reproduction: Asexual reproduction of ESFIDECLO1', by way of stem cuttings, was first initiated in September of 2015 at a commercial greenhouse in 's-Gravenzande, the Netherlands. 'ESFIDECLO1' was subsequently propagated by way of meristematic tissue culture micropropagation. Through ten subsequent generations, the unique features of this cultivar have proven to be stable and true to type.

SUMMARY OF THE INVENTION

The cultivar 'ESFIDECLO1' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESFIDECLO1'. These characteristics in combination distinguish 'ESFIDECLO1' as a new and distinct *Ficus* cultivar:

1. *Ficus* 'ESFIDECLO1' exhibits an obovate to broad oblong plant profile; and
2. *Ficus* 'ESFIDECLO1' exhibits an abundance of dark green, glossy foliage with a light green abaxial surface and a prominent red main vein; and
3. *Ficus* 'ESFIDECLO1' exhibits foliage with an upright attitude and a somewhat arching aspect.

BOTANICAL DESCRIPTION OF THE PLANT

Figure 1:
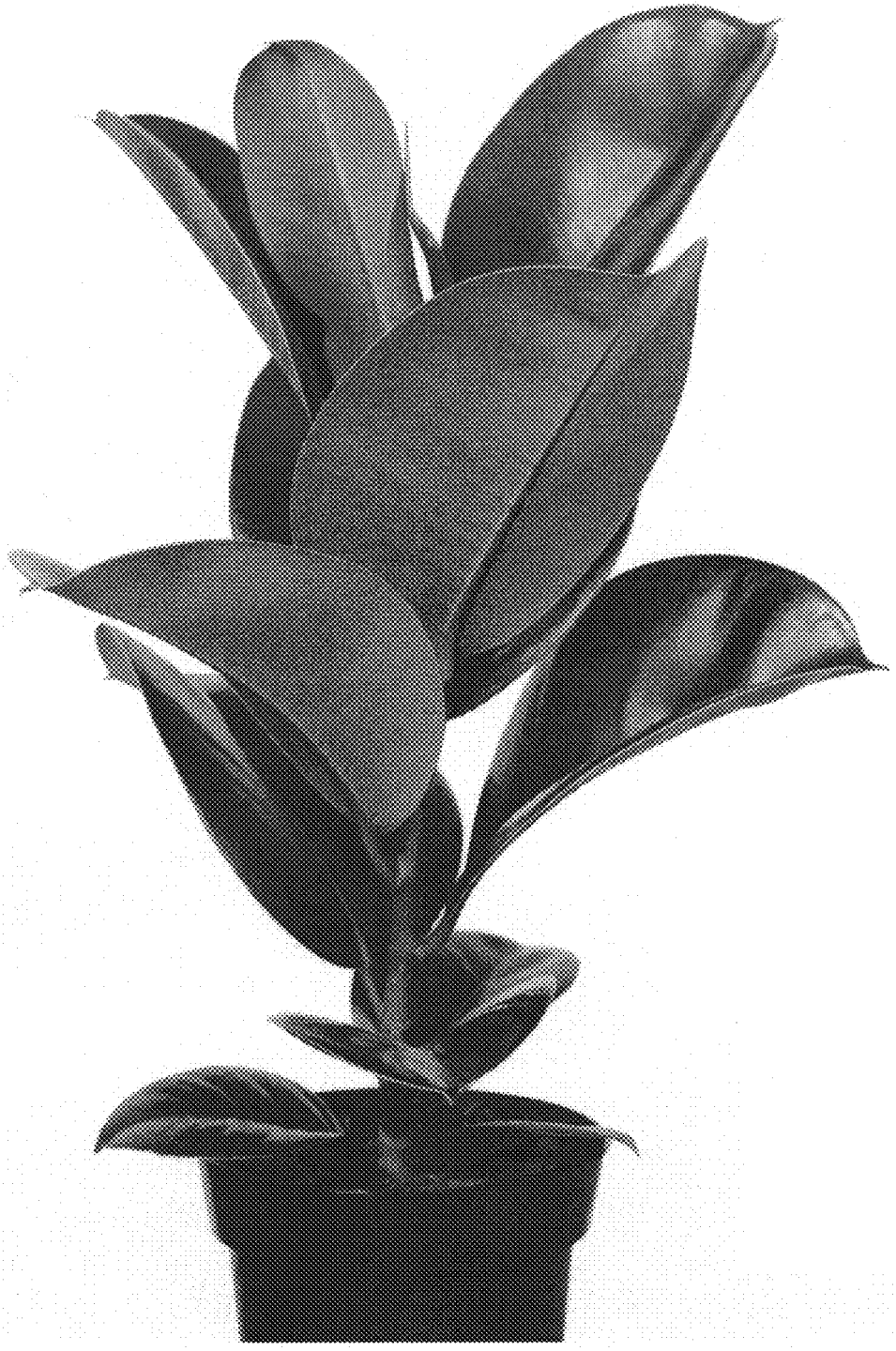
FIG. 1 illustrates, as nearly true as it is reasonably possible to make the same in color photographs of this type, an exemplary plant of 'ESFIDECLO1' grown in a commercial greenhouse in 's-Gravenzande, the Netherlands. This plant is approximately 25 weeks old, shown planted in a 19 cm container.
Figure 2:
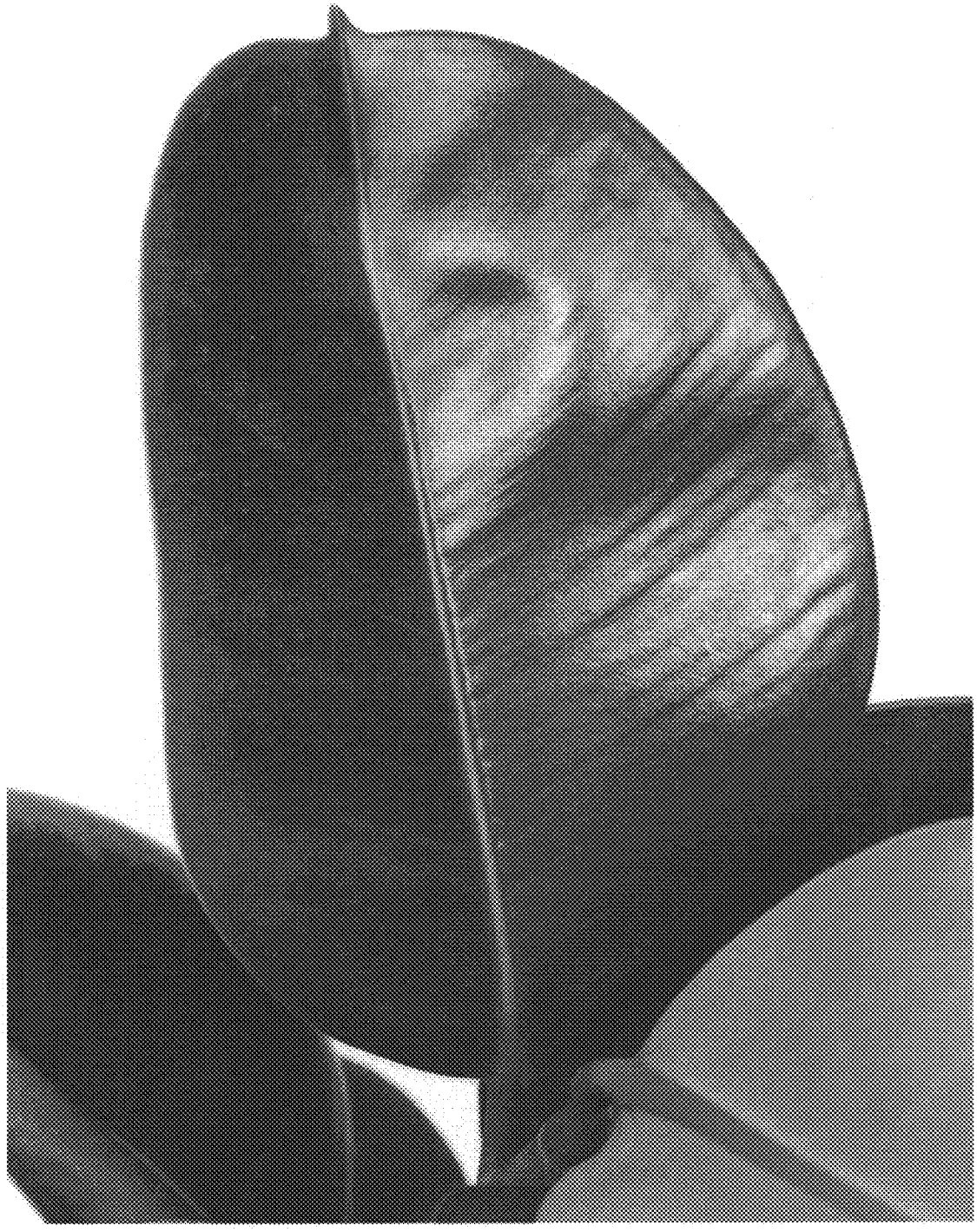
FIG. 2 illustrates, as nearly true as it is reasonably possible to make the same in color photographs of this type, the adaxial surface of the mature foliage of 'ESFIDECLO1'.
Figure 3:
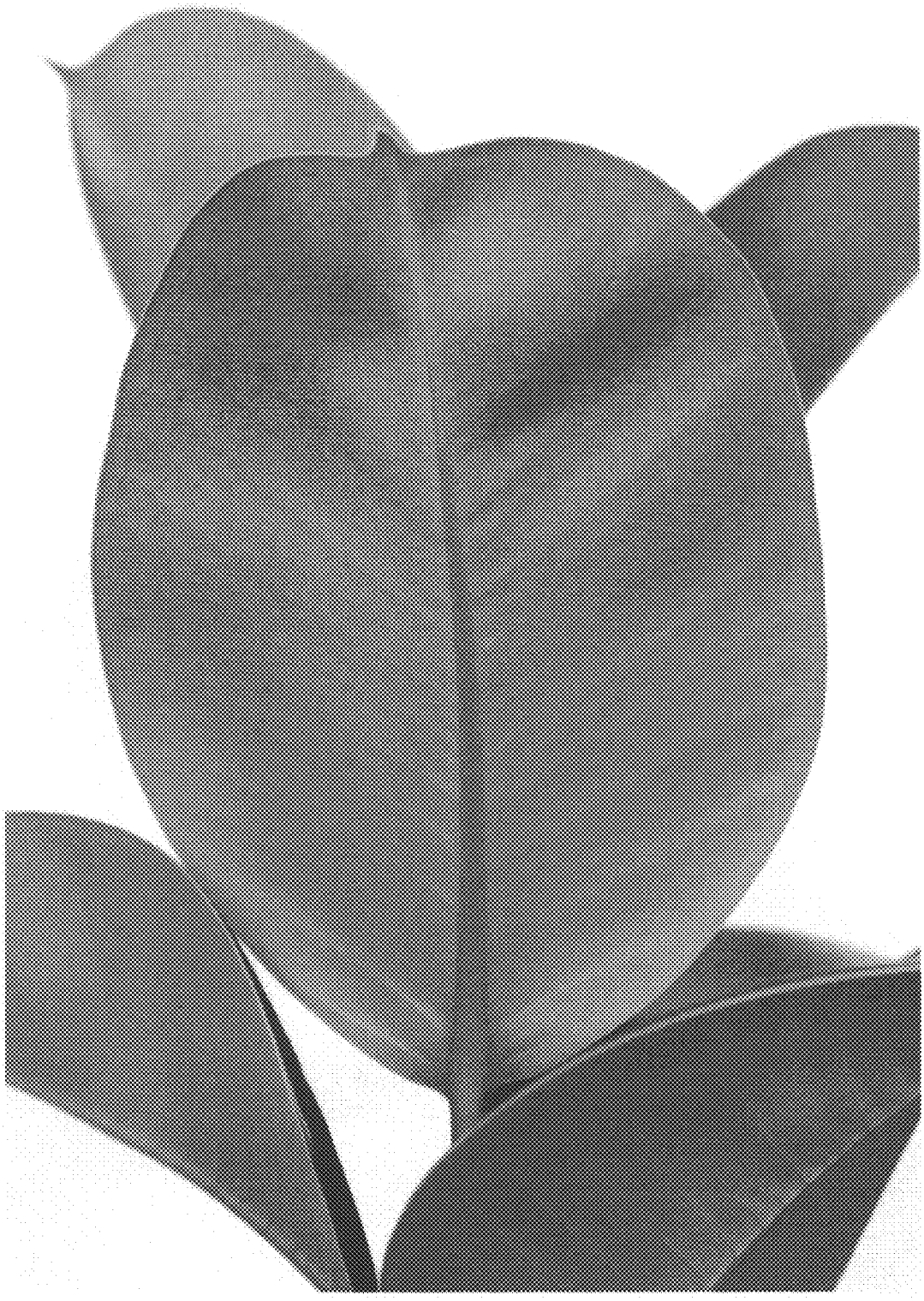
FIG. 3 illustrates, as nearly true as it is reasonably possible to make the same in color photographs of this type, the abaxial surface of the mature foliage of 'ESFIDECLO1'.

The following observations and measurements were made in August of 2020 and describe a sample set of six 25 week-old 'ESFIDECLO1' plants grown in 19 cm nursery pots, at a greenhouse in 's-Gravenzande, the Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESFIDECLO1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'ESFIDECLO1' and a comparison with the parent plant and most similar commercial variety of *Ficus* are provided below.

Plant description:

*Growth habit.*—Upright.

*Plant form.*—Obovate to broad oblong.

*Average height.*—39.2 cm from the soil level to the top of the foliar plane.

*Plant spread.*—Average of 30.7 cm.

*Growth rate.*—Moderately fast.

*Plant vigor.*—Moderately vigorous.

*Propagation type.*—Stem cuttings and meristematic tissue culture.

*Time to produce a rooted cutting.*—Approximately 40 days to produce a rooted cutting at approximately 25 degrees Celsius.

*Time to produce a finished plant.*—Approximately 18 weeks to produce a marketable finished plant in a 17 cm pot.

*Disease and pest resistance.*—Neither resistance nor susceptibility to typical *Ficus elastica* pests and diseases has been observed.

*Environmental tolerances.*—Adapt to, at least, USDA Zones 10 through 13 and temperatures as high as 40 degrees Celsius; moderate to high tolerance to rain; low to moderate tolerance to wind.

Root system:

*General.*—Moderately dense, moderately branched rooting; roots are slightly fibrous.

*Distribution in the soil profile.*—Moderately deep.

*Diameter of roots.*—1.5 mm on average.

*Texture.*—Smooth; no root hairs.

*Color.*—Greyed-yellow, nearest to RHS 162D.

Stems and branches:

*General branching habit.*—Basally branched main stems; no lateral branching. Pinching isn't required but will improve branching. Stems produce a milky exudate when damaged.

*Length.*—Approximately 23.4 cm.

*Diameter.*—Approximately 1.0 cm.

*Internode length.*—Approximately 2.4 cm.

*Attitude.*—Near vertical.

*Aspect.*—Rounded.

*Strength.*—Strong.

*Texture.*—Smooth, glabrous, and sparsely lenticellate; lenticels are 0.1 cm long and 0.05 cm wide, and colored greyed-orange, nearest to a mixture of RHS 164B and 164C.

*Luster.*—Very slightly glossy.

*Color, juvenile.*—Yellow-green, nearest to RHS 152B.

*Color, mature.*—Yellow-green, nearest to RHS 148A; stem surface exhibits a lighter shade of yellow-green when sheltered from ultraviolet light exposure, nearest to a mixture of RHS 146B and 146C.

*Color at the leaf nodes.*—Yellow-green, nearest to RHS 148A yet slightly darker; node surface exhibits a lighter shade of yellow-green when sheltered from ultraviolet light exposure, nearest to a mixture of RHS 146B and 146C. A thin radial band around the stem is also present at the nodes; average width of the band is 0.04 mm and is colored greyed-orange, nearest to RHS 164B.

*Color of the oldest wood.*—Nearest to in between yellow-green and greyed-green, RHS 147A and N189A yet slightly darker; axially striped greyed-orange, nearest to a mixture of RHS 164A and 164B.

Foliage:

*Arrangement.*—Alternate.

*Division.*—Simple.

*Quantity.*—10 leaves per main stem.

*Attitude.*—Upward and outward.

*Lamina.*—Shape — Broad ovate. Aspect — Moderately carinate; slightly arched. Dimensions — 18.5 cm long and 13.6 cm wide. Apex — Broad abruptly acute. Base — Rounded. Margin — Entire; slightly revolute. Texture of the adaxial surface — Smooth, glabrous. Small circular glands are randomly placed along the margins; glands are 0.03 cm wide and colored yellow-green, nearest to RHS 150D. Texture of the abaxial surface — Smooth and glabrous. Luster of the adaxial surface — Glossy. Luster of the abaxial surface — Matte to very slightly glossy. Color — Juvenile foliage, adaxial surface — Nearest to in between green and yellow-green, RHS 137A and 147A. Juvenile foliage, abaxial surface — Yellow-green, nearest to a mixture of RHS 144B, 146B and 146C; lightly suffused with a more yellowish coloration, nearest to RHS 152A. Mature foliage, adaxial surface — Nearest to in between green and greyed-green, RHS 137A and N189A yet slightly darker. Mature foliage, abaxial surface — Yellow-green, nearest to RHS 147B. Venation — Pattern — Pinnate. Color, adaxial surface — Nearest to in between yellow-green and greyed-brown, RHS 152B and 199B; nearest to 199B. Color, abaxial surface — Greyed-red, nearest to a mixture of RHS 178A and 178B. Petiole — Length — 1.7 cm. Diameter — Petioles flattened; 0.4 cm high and 0.6 cm wide. Strength — Strong. Texture — Smooth and glabrous. Luster — Moderately glossy. Color, adaxial surface — Greyed-green, nearest to RHS 197A yet slightly darker. Color, abaxial surface — Nearest to in between yellow-green and greyed-green, RHS 148A and 197A. Stipule — General — A single stipule is present at the base of each leaf, enveloping leaf buds prior to leaf opening; stipule drops away once leaf opens. Shape — Lanceolate. Length — 13.0 cm. Diameter — 2.3 cm. Aspect — Concave. Apex — Narrowly acute. Base — Broad cuneate. Margin — Entire. Texture, adaxial — Smooth and glabrous. Texture, abaxial — Smooth and glabrous. Color, adaxial surface — Yellow-green, nearest to RHS 152B. Color, abaxial surface — Yellow-green, nearest to RHS 152B.

Inflorescence: No flowering has been observed to date.

Comparison with the parent plant: Plants of the new cultivar 'ESFIDECLO1' differ from the parent, *Ficus elastica* 'Robusta' (not patented), which is also the most similar commercial variety known to the inventor, in the following characteristics described in Table 1 below.

TABLE 1

| Characteristic | 'ESFIDECLO1' | 'Robusta' |
|---|---|---|
| General plant profile. | Obovate to broad oblong. | Obovate. |
| Foliage apex. | Broad abruptly acute. | Acute. |
| Size of the main stems. | Larger than those of 'Robusta'. | Smaller than those of 'ESFIDECLO1'. |
| Abundance of foliage. | More abundant than 'Robusta'. | Less abundant than 'ESFIDECLO1'. |

TABLE 1-continued

| Characteristic | 'ESFIDECLO1' | 'Robusta' |
|---|---|---|
| Foliage size. | Larger than those of 'Robusta'. | Smaller than those of 'ESFIDECLO1'. |

That which is claimed is:

1. A new and distinct variety of *Ficus* plant named 'ESFIDECLO1', substantially as described and illustrated herein.

* * * * *